United States Patent [19]

Habenstein

[11] Patent Number: 5,585,247
[45] Date of Patent: Dec. 17, 1996

[54] FLUOROGENIC COMPOUNDS AND THEIR USE

[75] Inventor: Klaus Habenstein, Wetter, Germany

[73] Assignee: Behringwerke Aktiengesellschaft, Marburg, Germany

[21] Appl. No.: 526,001

[22] Filed: May 21, 1990

[30] Foreign Application Priority Data

May 23, 1989 [DE] Germany .......... 39 16 729.1

[51] Int. Cl.$^6$ .................................................. C12Q 1/34
[52] U.S. Cl. .................... 435/18; 435/805; 548/217; 548/179
[58] Field of Search .................. 435/18, 805; 548/217, 548/179

[56] References Cited

U.S. PATENT DOCUMENTS

| | | | |
|---|---|---|---|
| 4,826,989 | 5/1989 | Batz et al. .......... | 548/169 |
| 4,950,588 | 8/1990 | DaHagopta .......... | 436/805 |

FOREIGN PATENT DOCUMENTS

| | | | |
|---|---|---|---|
| 0024525 | 3/1981 | European Pat. Off. . | |
| 87959 | 2/1983 | European Pat. Off. .......... | C12Q 1/28 |
| 0137177 | 4/1985 | European Pat. Off. . | |
| 3248043 | 6/1984 | Germany . | |
| 58-129995 | 8/1983 | Japan .......... | C12Q 1/34 |
| WO87/02667 | 5/1987 | WIPO . | |
| WO90/00618 | 1/1990 | WIPO . | |

OTHER PUBLICATIONS

Suzuki et al., 28 Tetrahedron pp. 4075–4082 (1972).
The Periodic Table of the Elements.
Chem Abstracts (1987 Feb.) 106:172474f Chemiluminescence prolonged . . . .
Chem Abstracts (1987) 107:3671h New ultrasensitive detection.
Chem Abstracts (1987) 107:3100w New ultrasensitive detection system.
Chem Abstract (1981) 95:59678s Bioluminescent immunoassay.
Chem Abstracts 100:170894u (1984) Enhanced luminescent enzyme immunoassay.
Chem Abstracts 103(1985) 103:67626x Quantitation pg levels of specfic DNA.
Chem Abstracts (1985) 103:67631v Enhanced luminescence.
Titus et al (1973) An automated fluorescence method . . . Anal. Biochem 54:40–46.
Trepeta et al (1984 Feb.) Methylumbelliferyl BD Glucorone based Medium . . . J Clin Micro 19:172–4.
Aldrich Catalog p 759, entry 12,872–4 1986–1987.
White (1986) Medical Virology p 333 Academic Press.
Bailey et al., "On the Use of Fluorescent Labels in Immunoassay", Journal of Pharmaceutical & Biomedical Analysis, vol. 5, No. 7, (1987) pp. 649–658.
Soini et al., "Fluoroimmunoassay: Present Status and Key Problems", Clinical Chemistry, vol. 25, No. 3, (1979) pp. 353–361.
Wiley et al., "The Preparation of Thiazoles", Organic Reactions, 6, Chapter 8 (1951) pp. 367–409.
Cornforth, "Benzoxazoles and Related Systems", Chapter 6, (1957) pp. 418–451.
Schmidt, Richard, "Neue Methoden zur Glycosid– und Oligosaccharidsynthese—gibt es Alternativen zur Koenigs–Knorr–Method?", Angew. Chem. 98 (1986) pp. 213–236.
Seto et al., "Convenient Synthetic Method of 2–Carbamoyl–6–methoxybenzothiazole; One of Intermediates for the Synthesis of Firefly Luciferin", Bull. Chem. Society JPN, vol. 36, No. 3 (1963) pp. 331–333.
"Methods of Ensymology", vol. 13, 1986 pp. 20–22.

*Primary Examiner*—Michael P. Woodward
*Assistant Examiner*—Benet Prickril
*Attorney, Agent, or Firm*—Finnegan, Henderson, Farabow, Garrett & Dunner, L.L.P.

[57] ABSTRACT

The invention relates to fluorogenic compounds for the detection of hydrolyzing enzymes and the use of the fluorogenic compounds.

14 Claims, No Drawings

FLUOROGENIC COMPOUNDS AND THEIR USE

The invention relates to fluorogenic compounds for the detection of hydrolyzing enzymes and the use of the fluorogenic compounds.

Hydrolyzing enzymes, the so-called hydrolases, are responsible in the animal organism for a large number of reactions. A distinction is made here between hydrolases of various functions according to their specificity, such as, for example:

Esterases, such as, for example, acetylcholine esterase, which hydrolyze carbonyl esters.

Glycosidases, such as, for example, β-D-galactosidase, which hydrolyze the Q-glycosidic linkage of sugars to one another or to alcohols.

Phosphatases, such as, for example, alkaline phosphatase, which hydrolyze phosphoric acid esters.

Sulfatases, such as, for example, iduronate sulfarase, which hydrolyze sulfuric acid esters.

Hydrolases belong to the most important enzymes of the animal organism. Their absence or reduced or increased occurrence often indicates serious diseases of the organism. A known example is mucopolysaccharidosis; this recessively inherited disease, for which a distinction may be made between 7 different forms of manifestation, is based on a genetically determined defect of hydrolases, for example of β-galactosidase in the case of Morquio's disease and iduronate sulfatase in the case of Hunter's disease. Morquio's disease can be unambiguously diagnosed, for example, by determination of the β-D-galactosidase level of fibroblasts or leukocytes. The level of another glycosidase, amylase, in the blood or urine is used to diagnose pancreatic diseases. Hydrolytic enzymes are moreover used as diagnostic aids, so-called markers, for example in enzyme immunoassays.

Quantification of hydrolyzing enzymes for diagnostic purposes imposes the condition of highly sensitive and specific detection systems so that even low enzyme concentrations can be determined exactly. The naturally occurring substrates are unsuitable for the detection here, since hydrolysis products are already present in the samples before the test is carried out or the hydrolysis products are very difficult to determine. Synthetic substrates of which the hydrolysis products can be detected by physical or chemical means are therefore used in the prior art. As a rule, the detection is carried out by determination of the amounts of fluorescent or highly absorbing coloured substances released during the hydrolytic reaction. Chromogenic substances indeed have the advantage that they can also be perceived visually, that is to say without apparatus aids, and are thus accessible to direct evaluation. On the other hand, the sensitivity of chromogenic tests which can be achieved even with apparatus aids is not always adequate. The fluorescence measurement technique, which in general allows a signal output and therefore test sensitivity which is greater than that of chromogenic tests by a factor of $10^3$ to be achieved, has therefore been used for some time for high-sensitivity detections. The previous radioisotopes used as labels are therefore increasingly being replaced by fluorescence labels, especially in immunoassays (J. Pharm. Biomed. Anal. 5 (7), 1987, 649–58). The enzyme-amplified fluorescence measurement technique in particular opens up new paths for development of highly sensitive test methods here. However, as reported in the above literature citation, pages 651 and 652, and in Clin. Chem. 25 (3), 1979, 353–355, there are considerable difficulties in the general introduction of this promising measurement method as a result of insufficient fluorophores. Thus, for example, fluorescence dyestuffs of the fluorescein, rhodamine or resorufin type have an exceptionally low Stokes shift (difference between excitation and emission wavelength maximum) of about 20 nm. Although fluorophores of the umbelliferone type have a Stokes shift of about 70 am, they emit at too short a wavelength (450 nm), so that the intrinsic fluorescence of sample constituents and of carrier and vessel materials at about or above 400 nm falsifies the measurement results. Still other fluorophores do not have the hydroxyl group in the molecule which is essential for the above hydrolase substrates.

The present invention was therefore based on the object of providing fluorogenic compounds for the detection of hydrolyzing enzymes, hydrolysis of which leads specifically and highly sensitively to measurable fluorescence signals with maxima at about or above 500 am. This object is achieved according to the invention by a compound of the general formula I as the fluorogenic compound

in which

X is O or S,

R is a radical which can be split off by enzymatically catalyzed hydrolysis, $R_1$ is H, $C_1$ to $C_4$ alkyl or phenyl, which can be substituted by 1 to 3 —$CH_3$, and A has a molecular structure which lengthens the mesomerism of the benzoheterocyclic ring system, in particular includes aromatic or heteroaromatic and also substituted and optionally benzo-fused 6- and 5-membered ring systems which can also attack in the 2-position of the benzoheterocyclic radical via one or more multiple bonds, or an electron-withdrawing group, such as CN or $CF_3$.

Preferred compounds of the formula I are those in which

A is a phenyl or naphthyl radical, which is optionally substituted by 1 to 3 electronegative groups, such as, for example, —CN, —$CF_3$, thiazole or benzothiazole, or is a thiazole, oxazole, benzothiazole or benzoxazole radical which is optionally substituted by 1 to 3 electronegative groups, such as, for example, —CN or —$CF_3$.

Particularly preferred compounds are those in which

A is phenyl or phenyl which is substituted by up to 3 —CN, —$CF_3$, thiazole or benzothiazole radicals.

Compounds which are furthermore preferred are those in which

R is a carboxylic acid radical, a sugar radical, a phosphoric acid radical or a sulfuric acid radical, and particularly preferred compounds here are those in which the carboxylic acid is a $C_1$–$C_{10}$, and especially preferably a $C_1$–$C_3$, aliphatic carboxylic acid, an amino acid, especially preferably an alanine, which can also be derivatized, or an aromatic carboxylic acid.

Compounds in which the sugar is an α- or β-glucose or an α- or β-galactose are furthermore particularly preferred.

Compounds of the formula I in which $R^1$ is hydrogen are also preferred.

Surprisingly, it has been found that the fluorogenic compounds according to the invention react with hydrolysates of varying specificity, depending on the radical R selected. The excitation and emission maxima of the compounds are shifted towards shorter wavelengths by 60–90 nm in comparison with those of the associated free fluorophores. The Stokes shift between the particular excitation and emission maxima is up to 150 nm. The compounds according to the invention are prepared in a manner which is known per se by processes analogous to the literature from the fluorescence dyestuffs (literature: Org. Reactions, 6, 1951, Chapter 8 and Heterocyclic Compounds, Volume 5, 1957, Chapter 6) and the particular enzymatically degradable radical. Fluorogenic substrates for the detection of phosphatases and sulfatases are thus prepared by reaction of the fluorophore with suitable acid halides (for example phosphorus oxychloride or chlorosulfonic acid) by processes which are known per se. The carboxylic acid esters can be prepared from the carboxylic acid chlorides in a corresponding manner.

To prepare glycosides, the fluorescence dyestuffs are glycosylated by processes which are likewise known per se. The preparation of β-galactosides can be carried out, for example, by reaction of the corresponding fluorescence dyestuffs with α-D-acetobromogalactose and subsequent deacetylation. Glycosylation processes are described, for example, in Angew. Chemie 98, 1986, 213–236 and the literature quoted therein. Examples of glycosides which are obtainable by the processes mentioned are, for example, α- and β-D-galactopyranosides, α- and β-D-glucopyranosides and oligosaccharide derivatives derived therefrom and having 2–10, preferably 3–7, monosaccharide units.

The fluorogenic compounds according to the invention are used for the detection of various hydrolytic enzymes, for example carboxyl esterases, phosphatases, sulfatases and glycosidases. To detect the enzyme, the fluorogenic substrate is made available in a reagent mixture which contains any necessary buffer substances, stabilizers, activators, solubilizing agents, auxiliary enzymes or other auxiliary chemicals. These auxiliaries depend specifically on the reaction conditions, such as, for example, on the nature of the enzyme robe determined, as well as the substrate. The particular auxiliaries to be used are familiar to the expert. The various individual chemicals can be present side by side in a solution if they are of sufficient stability and chemical compatibility, but they can also be mixed with one another just before the detection reaction. After the reagent mixture has been brought together with the hydrolyzing enzyme to be detected or the biological sample to be tested the actual detection of the hydrolyrically active enzyme takes place by measurement of the fluorescence of the fluorescence dyestuff released from the corresponding fluorogenic substrate by the enzyme-catalyzed hydrolysis.

A reaction in solution, which can be carried out directly in a cell if appropriate and can be immediately evaluated by subsequent fluorescence photometric signal determination, is preferred in this context. Application of the fluorogenic substrates according to the invention to matrix-like, for example fibrous or film-like, reagent carriers which allow fluorescence photometric signal determination after the reaction has been carried out is likewise preferred.

The use of the compounds according to the invention as a substrate for enzyme immunoassays in which the hydrolase to be detected is covalently bonded to one partner of a specific bonding pair, for example to an antibody, a nucleic acid, a hormone and the like, is furthermore preferred. The conjugate can be free or in a form bonded to a solid phase here. Examples of solid phases are particulate phases, preferably latex particles or magnetizable particles.

The fluorogenic compounds according to the invention can be provided in various forms. Embodiments which already contain a combination of the fluorogenic substrates according to the invention with additional reagents needed for the test are preferred here. Examples of these are solutions, reagent tablets, powder mixtures or lyophilisates, if the detection reaction is subsequently to be carried out in solution. Alternatively, the fluorogenic substrates can likewise be absorbed onto an absorbent carrier or incorporated into hydrophilic and hygroscopic films, together with the additional reagents needed for the test.

The invention is illustrated by the following examples.

EXAMPLES

Example 1

Preparation of 2-phenyl-6-hydroxybenzoxazole 0.005 mol of 4-aminoresorcinol hydrochloride were dissolved in 7.5 ml of benzoyl chloride, while heating, and the solution was then boiled under reflux for 7 hours. The excess benzoyl chloride was subsequently distilled off in vacuo, 10 ml of ethanol were added to the residue and the mixture was boiled up briefly and, after cooling, rendered alkaline with 10 M NaOH solution. The alkaline solution was introduced into 200 ml of water and brought to pH 3 with concentrated hydrochloric acid, using a pH-meter. The crystal mass which precipitated here was filtered off with suction and recrystallized from 15 ml of toluene. The dried product (250 mg) was uniform according to thin layer chromatography (silica gel plate, ethyl acetate/glacial acetic acid 24:1).

Melting point.=214° C. (decomposition)

Fluorescence data:

|  | Excitation (nm) | Emission (nm) |
| --- | --- | --- |
| acid | 308 | 480 |
| basic | 370 | 480 |

Example 2

Preparation of 2-(4'-trifluoromethylphenyl)-6-hydroxybenzoxazole 1.5 ml (10 mol) of 4-trifluoromethylbenzoyl chloride were heated to 190° C. in an oil bath and 1.6 g (10 mmol) of 4-aminoresorcinol were added in portions. After 1 hour the reaction mixture was introduced into 100 ml of 10% strength sodium carbonate solution and heated. The unreacted acid chloride was hydrolyzed during this procedure. The product was then extracted with ethyl acetate and purified by column chromatography (silica gel 60, ethyl acetate or chloroform/glacial acetic acid 9:1).

Fluorescence data:

|  | Excitation (nm) | Emission (nm) |
| --- | --- | --- |
| basic | 380 | 520 |

The following products were obtainable by an analogous route:

| 2-(4'-cyanophenyl)-6-hydroxybenzoxazole (CPHB) | | |
| --- | --- | --- |
| basic | 390 | 540 |
| 2-(4'-pyridyl)-6-hydroxybenzoxazole | | |
| basic | 370 | 520 |

Example 3

Preparation of 2-cyano-6-hydroxybenzothiazole

Reference is made to Bull. Chem. Soc. Jpn. 36, 332 (1963) for the preparation.

Starting from commercially available 2-cyano-6-methoxybenzothiazole, the desired product was obtained by acid hydrolysis (Methods in Enzymology, Volume 13 (1986), page 20–21).

Yield (500 mg of methoxy compound employed): 130 mg of thin layer chromatography-pure product, mobile phase: chloroform/ethyl acetate 20/5.

Melting point: 208° C., decomposition.

Fluorescence data:

|  | Excitation (nm) | Emission (nm) |
|---|---|---|
| basic | 380 | 500 |

Example 4

Glycosylation reactions

A.) Galactosylation of 2-(4'-cyanophenyl)-6-hydroxybenzoxazole (CPHB)

0.01 mol of CPHB, 0.01 mol of acetobromogalactose, 5 mmol of $Ag_2O$ and 0.01 mol of calcium sulfate x ½ $H_2O$ were heated under reflux in 100 ml of dried toluene in a dry apparatus. (Quinoline can be added to the mixture as a reaction accelerator).

The reaction was carried out with exclusion of light and water (calcium chloride drying tube on the condenser), while stirring.

After a reaction time of 2 hours, the reaction was checked by thin layer chromatography. The CPHB acetogalactoside formed appeared as a dark blue fluorescent spot.

Mobile phases chloroform/ethyl acetate 4/1 or chloroform/acetone 4/1.

If the reaction was incomplete, further acetobromogalactose and $Ag_2O$ were added and the mixture was again heated under reflux.

When the reaction had ended, the reaction solution was filtered, the filter was washed with toluene and the washing toluene and mother liquor were combined and evaporated on a rotary evaporator at a maximum bath temperature of 40° C. under about 70 mbar.

The residue was dried in a vacuum drying cabinet at room temperature under 200 mbar. The impure product was purified by column chromatography. Separating agents silica gel 60 or Sephadex RPS. Mobile phases chloroform/ethyl acetate 4:1. The purified CPHB tetraacetylgalactoside was dried and its purity was checked by thin layer chromatography.

B.) Deacetylation of the acetylglycoside formed

The deacetylation was carried out in anhydrous methanol using sodium methylate. For this, the acetylglycoside (2 mg/dl) was dissolved in methanol and a little sodium methylate was added (5–10 µl of a 30% strength methanolic solution). The course of the deacetylation was monitored by means of thin layer chromatography.

Mobile phase: chloroform/ethyl acetate 4:1 and chloroform/methanol 3:1.

When the reaction had ended, the solution was rendered neutral to weakly acid with the ion exchanger Dowex 50× 8. The purity was checked by thin layer chromatography. Mobile phase: methanol/chloroform 1:3. The solution was then concentrated and the residue was dried.

C.) Glucosylation of CPHB 0.01 mol of Brigl's anhydride and 0.01 mol of CPHB were heated under reflux in 100 ml of toluene, while stirring and with exclusion of water. Reaction time: 24–48 hours The reaction was checked by thin layer chromatography. Mobile phase: chloroform/ethyl acetate 4:1.

The deacetylation was carried out as described under B. A β-glucoside with a weak dark blue fluorescence was obtained.

Example 5

Preparation of the acetic acid ester 50 mg of a benzoxazole derivative from Example 2 were dissolved in 10 ml of THF, and 1 ml of acetic anhydride and 100 µl of pyridine were added. After a reaction time of 1 hour, the reaction mixture was separated on preparative thin layer chromatography plates. Mobile phase: chloroform/glacial acetic acid 9:1.

The separation showed the acetate with a dark blue fluorescence in addition to unreacted starting substance with a whitish fluorescence. The acetate was obtained by elution of the corresponding silica gel zone.

Example 6

Preparation of the phosphoric acid ester 0.01 mol of 2-phenyl-6-hydroxybenzoxazole were dissolved in 20 ml of methylene chloride with 2 ml of diazabicycloundecene and the solution was cooled to –4° C. This solution was slowly pipetted into a mixture of 20 ml of pyridine and. 5 ml of phosphorus oxychloride at –4° C. and the mixture was left to stand at –4° C. for 2 hours, with occasional swirling. The reaction mixture was then introduced into 500 ml of 5% strength sodium bicarbonate solution and the mixture was stirred intensively for 1 hour and then freed from unreacted starting substance by several extractions with ethyl acetate. The aqueous solution was brought to pH 3 and concentrated to dryness and the desired phosphate was extracted from the salt mixture using methanol. Further purification was by chromatography (preparative thin layer chromatography, mobile phase ethyl acetate/water/methanol 100:25:30).

Example 7

Preparation of the N-toluenesulfonylalanine ester 0.01 mol of tosylalanine, 1.1 mmol of hydroxybenzothiazole and 1.1 mmol of dicyclohexylcarbodiimide (DCCI) were dissolved in succession in 2 ml of THF and the solution was stirred at room temperature for 30 minutes. 0.1 of CPHB (Example 2) was then dissolved in 1 ml of THF, the above solution was added and the mixture was stirred for 2 hours. A further 2 mmol of DCCI were then subsequently metered in and the reaction mixture was left to stand overnight.

Isolations:

The dicyclohexylurea formed was removed by centrifugation and the clear tetrahydrofuran solution was poured into ice-water. The aqueous phase thus formed was extracted three times with 50 ml of ethyl acetate and the combined extracts were concentrated in vacuo, after drying over sodium sulfate.

Purification:

The crude product was purified using a preparative thin layer chromatography plate (E. Merck). Mobile phase ethyl acetate

Example 8

Detection of leukocyte esterases

The methanolic extract, obtained in accordance with Example 7 from the preparative thin layer chromatography plate, of our desired product was applied to a filter paper preimpregnated with a 0.1 mol boric acid-hepes buffer, pH 7.5 and the filter paper was dried. Leukocytes in urine in a concentration of about 100 L/μl were indicated by the occurrence of a yellow fluorescence within 15 seconds after the sample had been dripped onto this indicator paper.

I claim:

1. A fluorogenic compound of the formula (I)

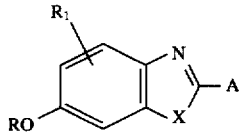

in which

X is O;

R is a radical which can be split off by enzymatically catalyzed hydrolysis;

$R_1$ is H, $C_1$- to $C_4$-alkyl or phenyl, which can be substituted by 1 to 3 —$CH_3$; and A is an aromatic, heteroaromatic, substituted and optionally benzo-fused 6- or 5-membered ring, or an electron withdrawing group;

said fluorogenic compound being fluorescent after R is split off by enzymatically catalyzed hydrolysis.

2. The compound as claimed in claim 1, wherein A is CN or $CF_3$.

3. The compound as claimed in claim 1, wherein

A is a radical selected from the group consisting of: a phenyl, naphthyl, thiazole, oxazole, benzothiazole, or benzoxazole, wherein the radical of A is optionally substituted by 1 to 3 electronegative groups.

4. The compound as claimed in claim 3, wherein the electronegative group is selected from the group consisting of —CN, —$CF_3$, thiazole, and benzothiazole.

5. The compound as claimed in claim 1, wherein

A is phenyl, optionally substituted by 1 to 3 radicals selected from the group consisting of: —CN, —$CF_3$, thiazole and benzothiazole radicals.

6. The compound as claimed in claim 1, wherein

R is a $C_1$–$C_{10}$-aliphatic carboxylic acid, an amino acid, an aromatic carboxylic acid, a phosphoric acid radical or a sulfuric acid radical.

7. The compound as claimed in claim 6, wherein R is a $C_1$–$C_3$ aliphatic carboxylic acid.

8. The compound as claimed in claim 6, wherein the amino acid is an alanine or a derivatized alanine.

9. The compound as claimed in claim 1, wherein $R_1$ is H.

10. A fluorescent measurement method for detecting a hydrolase, comprising bringing together a fluorogenic compound of the formula (I)

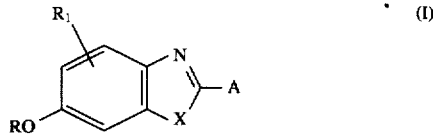

in which

X is O;

R is a radical which can be split off by enzymatically catalyzed hydrolysis, $R_1$ is H, $C_1$- to $C_4$-alkyl or phenyl, which can be substituted by 1 to 3 —$CH_3$, and A is an aromatic, heteroaromatic, substituted and optionally benzo-fused 6- or 5-membered ring, or a electron withdrawing group, with the hydrolase to be detect; rendering said fluorogenic compound fluorescent by splitting off g by enzymatically catalyzed hydrolysis; and measuring fluorescence of the fluorescent compound released from the fluorogenic compound by said hydrolysis.

11. The method as claimed in claim 10, wherein the hydrolase is covalently bonded to a member of a specific bonding pair.

12. The method as claimed in claim 11, wherein the member of a specific bonding pair is an antibody, a nucleic acid, or a hormone.

13. The method as claimed in claim 10, wherein the hydrolase is bonded to a particulate phase.

14. The method as claimed in claim 13, wherein the particulate phase is latex or magnetizable particles.

* * * * *

UNITED STATES PATENT AND TRADEMARK OFFICE
CERTIFICATE OF CORRECTION

PATENT NO. : 5,585,247
DATED : December 17, 1996
INVENTOR(S) : Klaus HABENSTEIN

It is certified that error appears in the above-indentified patent and that said Letters Patent is hereby corrected as shown below:

Claim 10, column 8, line 27, "0;" should read --0,--.

Claim 10, column 8, lines 33-34, "a electron withdrawing" should read --an electron-withdrawing--.

Claim 10, column 8, line 34, "detect" should read --detected--.

Claim 10, column 8, line 36, "g" should read --R--.

Signed and Sealed this

Sixteenth Day of September, 1997

Attest:

BRUCE LEHMAN

Attesting Officer

Commissioner of Patents and Trademarks